(12) United States Patent
Leeuwen et al.

(10) Patent No.: US 8,912,346 B2
(45) Date of Patent: Dec. 16, 2014

(54) PALLADIUM PHOSPHINE COMPLEXES FOR THE TELOMERIZATION OF BUTADIENE

(75) Inventors: Petrus Van Leeuwen, Kockengen (NL); Mathieu Tschan, Tarragona (ES); Eduardo Jose Garcia-Suarez, Oviedo (ES); Zoraida Freixa, Tarragona (ES); Henk Hagen, Terneuzen (NL)

(73) Assignee: Dow Global Technologies LLC, Midland, MI (US)

( * ) Notice: Subject to any disclaimer, the term of this patent is extended or adjusted under 35 U.S.C. 154(b) by 530 days.

(21) Appl. No.: 13/263,353

(22) PCT Filed: May 14, 2009

(86) PCT No.: PCT/ES2009/070159
§ 371 (c)(1),
(2), (4) Date: Oct. 7, 2011

(87) PCT Pub. No.: WO2010/130846
PCT Pub. Date: Nov. 18, 2010

(65) Prior Publication Data
US 2012/0046475 A1    Feb. 23, 2012

(51) Int. Cl.
*C07F 9/28*       (2006.01)
*C07F 9/02*       (2006.01)
*C07C 5/00*       (2006.01)
*C07C 2/24*       (2006.01)
*C07C 2/34*       (2006.01)
*C07C 2/02*       (2006.01)
*C07F 9/655*      (2006.01)

(52) U.S. Cl.
CPC .................................. *C07F 9/65522* (2013.01)
USPC ............. 549/220; 556/404; 568/12; 585/251; 585/510; 585/512; 585/514; 585/520; 585/527; 585/531

(58) Field of Classification Search
USPC .......... 549/220; 585/510, 514, 520, 527, 531, 585/251; 556/404; 568/12
See application file for complete search history.

(56) References Cited

U.S. PATENT DOCUMENTS

| | | |
|---|---|---|
| 5,254,782 A | 10/1993 | Schaart et al. |
| 7,026,523 B2 | 4/2006 | Rottger et al. |
| 7,030,286 B2 | 4/2006 | Rottger et al. |
| 7,141,539 B2 | 11/2006 | Edwards |
| 7,368,597 B2 | 5/2008 | Gaemers et al. |
| 7,371,909 B2 | 5/2008 | Beller et al. |
| 7,425,658 B2 | 9/2008 | Edwards |
| 7,541,506 B2 | 6/2009 | Roettger et al. |
| 2005/0038305 A1 | 2/2005 | Edwards |
| 2007/0004939 A1 | 1/2007 | Volland et al. |
| 2011/0137086 A1 | 6/2011 | Briggs et al. |

FOREIGN PATENT DOCUMENTS

| | | |
|---|---|---|
| EP | 561779 A1 | 9/1993 |
| WO | 2006024614 A1 | 3/2006 |
| WO | 2006024615 A1 | 3/2006 |
| WO | 2006024616 A1 | 3/2006 |
| WO | 2007085321 A1 | 8/2007 |

OTHER PUBLICATIONS

Jackstell, Highly Efficient Catalyst for the Telomerization of 1,3-Dienes with Alcohols, Angew. Chem., Int. Ed. 2002, 986-989,41, 6, Wiley-VCH Verlag GmbH, Germany.
Jackstell, Efficient telomerization of 1,3-butadiene with alcohols, J. of Mol. Catalysis, 2002, 105-112, 185.
Jackstell, An Industrially Viable Catalyst System for Palladium-Catalyzed Telomerizations of 1,3-Butadiene with Alcohols, Chem. Eur J., 2004, 3891-3900, 10, Wiley-VCH Verlag Gmbh & Co. KGaA, Weinheim.
PCT/US09/051347, International Search Report and Written Opinion.
PCT/US09/051347, International Preliminary Report on Patentability.

*Primary Examiner* — T. Victor Oh

(57) ABSTRACT

A phosphine ligand suitable for use in telomerizing butadiene comprises two phenyl groups and a xanthene moiety.

7 Claims, No Drawings

PALLADIUM PHOSPHINE COMPLEXES FOR THE TELOMERIZATION OF BUTADIENE

Production of 1-octene via telomerization of butadiene typically occurs when methanol is present with a palladium-phosphine based catalyst in a three step process. In step 1, telomerization of butadiene yields 1-methoxy-2,7-octadiene (MOD-1). In step two, hydrogenation of MOD-1 yields methyloctylether. In step three, methyloctylether undergoes ether cleavage to yield 1-octene and methanol.

A catalytic telomerization combination of a palladium (Pd) salt and triphenylphosphine (TPP) provides less than desirable results in terms of 1-octene yield. This appears to be due, at least in part, to side reactions that lead to formation of 3-methoxy-1,7-octadiene (MOD-3) and 1,3,7-octatriene.

Those who produce 1-octene via butadiene telomerization desire a telomerization catalyst with higher productivity in terms of kilogram (kg) of MOD-1 produced per gram (g) of Pd catalyst largely because of Pd cost.

Skilled artisans recognize from the teachings set forth in European Patent publication (EP) 461222 and EP 561779 that aryl-phosphine ligands with ortho-methoxide substituents tend to enhance selectivity to MOD-1 over side reaction products such as MOD-3 and 1,3,7-octatriene. The increased selectivity is offset by lower Pd complex stability as evidenced by at least one of lower catalyst productivity and increased Pd losses (e.g. via precipitation), especially as methanol (MeOH) concentration increases.

U.S. Pat. No. 7,425,658 (Edwards) discloses a method for producing 1-octene from butadiene by dimerizing and alkoxylating butadiene in the presence of one or more alkoxy substituted phosphine ligands under alkoxydimerization conditions with an alkoxydimerization catalyst. Illustrative phosphine ligands include tris-(2,4,6-trimethoxy phenyl) phosphine and tris-(4-methoxyphenyl) phosphine.

U.S. Provisional Patent Application (USPPA) 61/088,186, filed 12 Aug. 2008 (Briggs et al.) teaches telomerization of 1,3-butadiene in the presence of an organic hydroxy compound, a palladium catalyst and a phosphine ligand. Illustrative phosphine ligands include tris-(2-methoxyphenyl)phosphine, tris-(2,4-dimethoxyphenyl)phosphine, bis-(2-methoxyphenyl)phenylphosphine, tris-(2-methoxy-4-fluorophenyl)phosphine, and tris-(2-methoxy-4-chlorophenyl)phosphine.

U.S. Pat. No. 7,026,523 (Röttger et al.) provides a method for telomerizing non-cyclic olefins that includes use of a palladium carbene complex as a catalyst.

In some aspects, this invention is a phosphine ligand suitable for use in Pd-catalyzed telomerization of butadiene to MOD-1. The phosphine ligand comprises two phenyl groups, a xanthene, the xanthene having an oxygen atom incorporated into a rigid ring structure consisting of two aromatic rings, and a linking phosphorous moiety, the ligand being represented by a formula as follows:

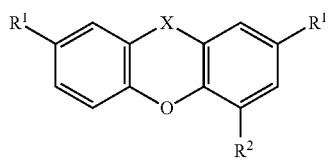

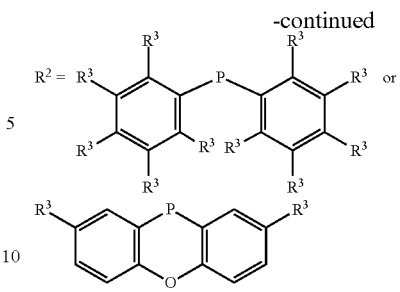

wherein, $R^1$ are the same and are each H, linear, branched or cyclic $C_1C_{20}$ alkyl, $C_6$-$C_{18}$ aryl, $C_1$-$C_{20}$ alkoxy or polyether. All $R^3$ are the same of dissimilar, and are each H, linear, branched or cyclic $C_1$-$C_{20}$ alkyl, $C_6$-$C_{18}$ aryl, halogen, trifluoromethyl, $C_1$-$C_{20}$ alkoxy, or $C_1$-$C_{20}$ dialkylamino. X is a bridging moiety consisting of either a dimethyl-substituted carbon (—$CMe_2$-) or silicon (—$SiMe_2$) atom.

In some aspects, this invention is a process for synthesizing the xanthene-containing phosphine ligand, the process comprising sequential steps a) monobrominating a xanthene, b) lithiating the monobrominated xanthene, and c) effecting nucleophilic substitution of the lithiated, monobrominated xanthene using a phosphine. Recovery of the ligand occurs via conventional technology, e.g. filtration and solvent removal. Preferred reactants include 2,7-di-tert-butyl-9,9-dimethyl-9H-xanthene as the xanthene and chlorodiphenyl phosphine as the phosphine.

In some aspects, this invention is a process for producing 1-octene which comprises steps: (i) reacting 1,3-butadiene with a primary aliphatic alcohol or aromatic hydroxy compound having formula R—H, in the presence of a telomerization catalyst comprising palladium and a phosphine ligand represented by the above formula to form a 1-substituted-2,7-octadiene of formula $CH_2$=CH—$CH_2$—$CH_2$—$CH_2$—CH=CH—$CH_2$—R, in which R represents a residue of the primary aliphatic alcohol or aromatic hydroxy compound; (ii) subjecting the 1-substituted-2,7-octadiene formed in step (i) to hydrogenation in the presence of a hydrogenation catalyst to form a 1-substituted octane of formula $CH_3$—$CH_2$—$CH_2$—$CH_2$—$CH_2$—$CH_2$—$CH_2$—$CH_2$—R; and (iii) decomposing the 1-substituted octane formed in step (ii) in the presence of a suitable catalyst to form 1-octene. The primary aliphatic alcohol is suitably methanol or ethanol. The catalyst for step (iii) is desirably an alumina catalyst.

Processes for producing 1-octene from a telomerization product mixture comprising the 1-substituted-2,7-octadiene are known; see e.g., U.S. Patent Application Publication 2005/0038305 and U.S. Pat. No. 7,030,286.

Step (i) preferably occurs in a reaction fluid that comprises the 1,3-butadiene, the hydroxy compound, and the telomerization catalyst. The reaction fluid may further comprise one or more optional component(s), such as an organic solvent, a catalyst promoter, a catalyst stabilizer, or a butadiene polymerization inhibitor. The phosphine ligand is preferably present in an amount sufficient to stabilize palladium. The amount advantageously provides an initial ligand to palladium ratio of at least 1.0, preferably at least 1.5. The initial phosphine ligand to palladium ratio is advantageously less than 50, and preferably less than 40.

The process for producing 1-octene can employ any palladium catalyst or catalyst precursor known in the art, e.g. palladium metal, a palladium(II) compound, a palladium(0) complex, or a mixture thereof.

The process for producing 1-octene advantageously occurs under an inert atmosphere, such as nitrogen, argon, or helium, and at a reaction temperature sufficient to produce the 1-substituted-2,7-octadiene. The reaction temperature is preferably greater than (>) 40° centigrade (° C.), more preferably >50° C., and still more preferably >60° C., and is preferably below (<) 120° C., more preferably <110° C., and still more preferably <100° C.

When ranges are stated herein, as in a range of from 2 to 10, both end points of the range (e.g. 2 and 10) and each numerical value, whether such value is a rational number or an irrational number, are included within the range unless otherwise specifically excluded.

The term "comprising" and derivatives thereof does not exclude the presence of any additional component, step or procedure, whether or not the same is disclosed herein. In order to avoid any doubt, all compositions claimed herein through use of the term "comprising" may include any additional additive, adjuvant, or compound whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or", unless stated otherwise, refers to the listed members individually as well as in any combination.

Expressions of temperature may be in terms either of degrees Fahrenheit (° F.) together with its equivalent in ° C. or, more typically, simply in ° C.

Unless stated to the contrary, implicit from the context, or customary in the art, all parts and percents are based on weight.

For purposes of United States patent practice, the contents of any patent, patent application, or publication referenced herein are hereby incorporated by reference in their entirety (or the equivalent US version thereof is so incorporated by reference) especially with respect to the disclosure of synthetic techniques, definitions (to the extent not inconsistent with any definitions provided herein) and general knowledge in the art.

Descriptions and examples serve to illustrate, rather than define or limit, this invention in any way and do not constitute an exhaustive or all-inclusive listing of all possible embodiments of this invention. To those skilled in the art, other embodiments within the scope of appended claims will be apparent, from consideration of the specification and/or practice of the invention as disclosed herein.

Ligand synthesis occurs via a multi-step process. In step one, monobrominate a xanthene, preferably 2,7-di-tert-butyl-9,9-dimethyl-9H-xanthene. In step two, lithiate the monobrominated xanthene. In step three, effect nucleophilic substitution of the monolithiated xanthene using a phosphine, preferably chlorodiphenylphosphine. In step four, effect ligand recovery, e.g. by filtration and solvent removal.

Example 1

Add 11 molar equivalents of NBS (N-bromosuccinimide) to a flask that contains a solution of 2.87 grams (g) of 2,7-di-tert-butyl-9,9-dimethyl-9H-xanthene in 100 mL of a 1:1 volumetric mixture of DMF (dimethylformamide) and tetrahydrofuran (THF). Cover the flask with aluminum foil and stir its contents overnight.

Monitor conversion of 2,7-di-tert-butyl-9,9-dimethyl-9H-xanthene to 4-bromo-2,7-tert-butyl-9,9-dimethyl-9H-xanthene (mono-brominated product) by gas chromatographic (GC) daily, adding sufficient NBS as needed to maintain a molar excess of NBS. After four days and a total NBS addition of fourteen (14) molar equivalents, GC analysis reveals two peaks, one for the starting xanthene and one for mono-brominated and di-brominated products in a molar ratio of starting xanthene to mono-brominated product to di-brominated product of 7:90:3.

Recover solid contents of the flask by evaporating solvent to dryness. Wash the solid with water and then extract crude product with diethylether. Evaporate the diethyl ether to yield a yellow solid. Purify the yellow solid by filtration over silica with hexane as eluent to yield 2.8 g of a white solid product that contains 90 mole percent (mol %) of monobrominated product, 7 mol % of the starting xanthene and 3 mol % of dibrominated product, each mol % being based upon combined moles of monobrominated product, starting xanthene, and dibrominated product. Use this product without further purification in phosphine synthesis.

Slowly add, with stirring, 1.1 molar equivalents of 2.5 molar n-butyllithium (n-BuLi) to a solution of 1.53 g of the white solid product (3.44 millimoles (mmol) of monobrominated product) in 30 milliliters (mL) of THF that is maintained at a set point temperature of −78° C. Maintain the set point temperature and continue stirring for one hour before adding one (1) equivalent (0.67 mL) of chlorodiphenyl phosphine. Continue stirring for one hour at the set point temperature and then for an additional hour at room temperature (nominally 25° C.).

Evaporate solvent under vacuum to yield a wet solid, then add 20 mL of dichloromethane to the wet solid to form a solution and then filter the solution and evaporate the solvent to yield a white solid.

Purify the white solid via chromatography on a silica gel column using a 4:1 volume ratio mixture of hexane and dichloromethane as eluent. The purified solid (0.95 g or 1.87 mmol represents a 55% yield, based upon starting materials) and is 4-(diphenylphosphino)-2,7-tert-butyl-9,9-dimethyl-9H-xanthene (1).

Example 2

Replicate Example 1 with changes to synthesize 4-(di-p-trifluoromethylphenylphosphino)-2,7-di-tert-butyl-9,9-dimethylxanthene. Substitute 1.2 g (3.44 mmol) of chloro-bis-p-trifluoromethylphenylphosphine for the chlorodiphenyl phosphine used in Example 1. Use 1.53 g (3.44 mmol) of the white solid product that contains 90 mole percent (mol %) of monobrominated product. Change the volume ratio mixture on the silica gel column to 8:1. The purified solid represents a yield of 55%.

Example 3

Replicate Example 2 with changes to synthesize 4-(di-p-tolylphosphino)-2,7-di-tert-butyl-9,9-dimethylxanthene. Substitute 0.86 g (3.44 mmol) of chloro-bis-p-tolylphosphine for the chloro-bis-p-trifluoromethylphenylphosphine used in Example 2. Change the volume ratio mixture on the silica gel column to 10:3. The purified solid represents a yield of 56%.

Example 4

Replicate Example 3 with changes to synthesize 4-(di-p-methoxyphenylphosphino)-2,7-di-tert-butyl-9,9-dimethylxanthene. Substitute 0.97 g (3.44 mmol) of chloro-bis-p-methoxyphenylphosphine for the chloro-bis-p-tolylphosphine used in Example 3. Change the volume ratio mixture on the silica gel column to 1:1. The purified solid represents a yield of 28%.

Example 5

Replicate Example 4 with changes to synthesize 4-(2,7-dimethylphenoxaphosphino)-2,7-di-tert-butyl-9,9-dimethylxanthene. Substitute 0.90 g (3.44 mmol) of chloro-2,7-dimethylphenoxaphosphine for the chloro-bis-p-methoxyphenylphosphine used in Example 4. Change the volume ratio mixture on the silica gel column to 5:1. The purified solid represents a yield of 58%.

Butadiene Telomerization Tests

Conduct testing in a 1 liter (L) Parr reactor (electropolished stainless steel, maximum working pressure 131 bar or 13,100 KPa, temperature range of from −10° C. to 350° C., and stirring speed range of from 0 revolutions per minute (rpm) to 1200 rpm). For each reaction, fill the Parr reactor's autoclave with specified amounts of methanol, promoter (sodium methoxide, at a promoter to palladium molar ratio of 5 to 1) and inhibitor (diethyl hydroxylamine, approximately 20 parts by weight per million parts by weight (ppm) based on total weight of methanol plus crude $C_4$ load). Close the autoclave, purge it twice with low pressure nitrogen (6 bar or 600 kilopascals (KPa)) to substantially remove oxygen contained in the autoclave. Pressurize the autoclave once with high pressure nitrogen (20 bars or 2,000 KPa) to test for leaks.

After the leak test, fill a stainless steel sample cylinder with a crude $C_4$ stream that contains approximately 50 wt % 1,3-butadiene, based upon total crude $C_4$ stream weight and pressure add the stream to the autoclave with low pressure nitrogen (6 bar or 600 KPa). Raise the temperature in the autoclave to a desired work temperature (60° C., 75° C., 90° C. or 100° C. as shown in Table 1 below).

For Comparative Example A, use a standard catalyst, palladium acetyl acetonate ($Pd(acac)_2$) plus two molar equivalents of triphenyl phosphine and one molar equivalent of acetic acid. Prepare the catalyst in methanol by dissolving all three components such that the palladium concentration in methanol equals about 500 ppm. For Examples 1-5, replicate Comparative Example A, but substitute the xanthene-based ligand for triphenyl phosphine.

Weigh an amount of catalyst solution, such that the palladium concentration in the reactor after addition of all raw materials is 10 ppm based upon total weight of raw materials, into a dry box then place the catalyst solution into a stainless steel sample cylinder. Pressure add the catalyst solution to the autoclave using high pressure nitrogen (19 bars to 20 bars or 1900 KPa to 2000 KPa). Following catalyst addition, a reaction begins, producing a final product. Take samples from the autoclave at set times (five minutes after catalyst addition and at 30 minute intervals thereafter) and analyze gas and liquid phases of the samples via GC.

Determine palladium precipitation in the reactor by measuring palladium concentration in the liquid phase after the reaction and comparing that to a theoretical number based on total amount of palladium added and total liquid volume which includes liquids added at the beginning of the reaction and liquids formed due to the butadiene conversion. Measure palladium concentration in the liquid using Inductively Coupled Plasma Atomic Emission Spectroscopy (ICP-AES).

Table 1 below presents data for, respectively Conversion, Selectivity to MOD-1 and Pd Precipitation, all at methanol (MeOH) to butadiene (Bd) weight ratios of 2, 2.6 and 5.

TABLE 1

1,3-butadiene conversion, selectivity to MOD-1 and palladium precipitation

| Ligand | Temp. (° C.) | MeOH/Bd (wt/wt) | Bd conv. (%) | MOD-1 selectivity (%) | Pd precip. (%)* |
|---|---|---|---|---|---|
| Comparative Example A | 60 | 2 | 32 | 91 | −3 |
| | 60 | 2.6 | 29 | 92 | 8 |
| | 60 | 5 | 17 | 92 | 3 |
| | 75 | 2.6 | 62 | 88 | 0 |
| | 90 | 2 | 82 | 80 | 16 |
| | 90 | 2.6 | 85 | 83 | 17 |
| | 100 | 2 | 84 | 73 | 18 |
| Example 1 | 60 | 2 | 40 | 94 | −2 |
| | 60 | 2.6 | 36 | 94 | 2 |
| | 60 | 5 | 33 | 94 | −4 |
| | 75 | 2.6 | 67 | 93 | n.d. |
| | 90 | 2 | 89 | 88 | 2 |
| | 90 | 2.6 | 93 | 89 | 6 |
| | 100 | 2 | 91 | 84 | 2 |
| | 110 | 2 | 90 | 81 | 6 |
| | 120 | 2 | 88 | 78 | 37 |
| Example 2 | 60 | 2 | 52 | 90 | −7 |
| | 60 | 2.6 | 62 | 92 | 2 |
| | 60 | 5 | 63 | 93 | 8 |
| | 75 | 2.6 | 73 | 86 | 16 |
| | 90 | 2 | 67 | 72 | 17 |
| | 90 | 2.6 | 75 | 77 | 20 |
| | 100 | 2 | 72 | 61 | 29 |
| Example 3 | 60 | 2 | 49 | 94 | 3 |
| | 60 | 2.6 | 34 | 94 | 1 |
| | 60 | 5 | 19 | 93 | 3 |
| | 75 | 2.6 | n.d. | n.d. | n.d. |
| | 90 | 2 | 92 | 89 | 10 |
| | 90 | 2.6 | 93 | 90 | 14 |
| | 100 | 2 | 93 | 86 | 14 |
| Example 4 | 60 | 2 | 36 | 94 | −8 |
| | 60 | 2.6 | 22 | 94 | 2 |
| | 60 | 5 | 15 | 93 | 13 |
| | 75 | 2.6 | n.d. | n.d. | n.d. |
| | 90 | 2 | 92 | 90 | 20 |
| | 90 | 2.6 | 91 | 90 | 14 |
| | 100 | 2 | 91 | 85 | 22 |
| Example 5 | 60 | 2 | 32 | 93 | 1 |
| | 60 | 2.6 | 12 | 85 | −4 |
| | 60 | 5 | 13 | 79 | 5 |
| | 75 | 2.6 | n.d. | n.d. | n.d. |
| | 90 | 2 | 82 | 89 | 0 |
| | 90 | 2.6 | 83 | 91 | 10 |
| | 100 | 2 | 87 | 87 | 5 | n.d. means not determined;
*Estimated error of 5% absolute for all readings

The data presented in Table 1 above demonstrate that the xanthene-containing phosphine ligand of various aspects of this invention provides results in terms of 1,3-butadiene conversion, selectivity to MOD-1 and Pd precipitation that are better than that provided by a conventional triphenyl phosphine ligand under identical operating conditions.

What is claimed is:

1. A phosphine ligand, the ligand comprising two phenyl groups, a xanthene, the xanthene having an oxygen atom incorporated into a rigid ring structure consisting of two aromatic rings, and a linking phosphorous moiety, the ligand being represented by a formula as follows:

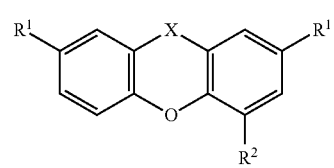

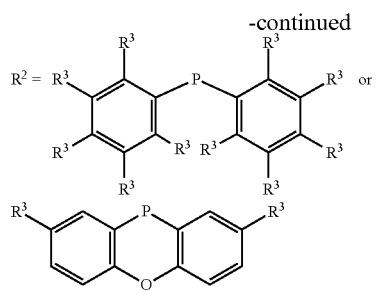

wherein, R¹ are the same and are each H, linear, branched or cyclic $C_1$-$C_{20}$ alkyl, $C_6$-$C_{18}$ aryl, $C_1$-$C_{20}$ alkoxy or polyether. All R³ are the same or dissimilar, and are each H, linear, branched or cyclic $C_1$-$C_{20}$ alkyl, $C_6$-$C_{18}$ aryl, halogen, trifluoromethyl, $C_1$-$C_{20}$ alkoxy, or $C_1$-$C_{20}$ dialkylamino. X is a bridging moiety selected from a dimethyl-substituted carbon (—CMe₂-) and silicon (—SiMe₂) atom.

2. The phosphine ligand of claim 1, wherein the ligand is 4-(diphenylphosphino)-2,7-tert-butyl-9,9-dimethyl-9H-xanthene.

3. The phosphine ligand of claim 1, wherein the ligand is 4-(di-p-trifluoromethylphenylphosphino)-2,7-di-tert-butyl-9,9-dimethylxanthene.

4. The phosphine ligand of claim 1, wherein the ligand is 4-(di-p-tolylphosphino)-2,7-di-tert-butyl-9,9-dimethylxanthene.

5. The phosphine ligand of claim 1, wherein the ligand is 4-(di-p-methoxyphenylphosphino)-2,7-di-tert-butyl-9,9-dimethylxanthene.

6. The phosphine ligand of claim 1, wherein the ligand is 4-(2,7-dimethylphenoxaphosphino)-2,7-di-tert-butyl-9,9-dimethylxanthene.

7. A process for producing 1-octene which comprises steps: (i) reacting 1,3-butadiene with a primary aliphatic alcohol aromatic hydroxyl compound having formula R—H, in the presence of a telomerization catalyst comprising palladium and the phosphine ligand of claim 1 to form a 1-substituted-2,7-octadiene of formula CH₂=CH—CH₂—CH₂—CH₂—CH=CH—CH₂—R, in which R represents a residue of the primary aliphatic alcohol aromatic hydroxy compound; (ii) subjecting the 1-substituted-2,7-octadiene formed in step (i) to hydrogenation in the presence of a hydrogenation catalyst to form a 1-substituted octane of formula CH₃—CH₂—CH₂—CH₂—CH₂—CH₂—CH₂—CH₂—R; and (iii) decomposing the 1-substituted octane formed in step (ii) in the presence of an alumina catalyst to form 1-octene.

* * * * *